US006198828B1

(12) United States Patent
Kuo

(10) Patent No.: US 6,198,828 B1
(45) **Date of Patent: *Mar. 6, 2001**

(54) OFF-LINE FEEDBACK PATH MODELING CIRCUITRY AND METHOD FOR OFF-LINE FEEDBACK PATH MODELING

(75) Inventor: Sen M. Kuo, DeKalb, IL (US)

(73) Assignee: Texas Instruments Incorporated, Dallas, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 08/992,699

(22) Filed: Dec. 17, 1997

Related U.S. Application Data

(60) Provisional application No. 60/033,104, filed on Dec. 17, 1996.

(51) Int. Cl.[7] .................................................. A61F 11/06

(52) U.S. Cl. ..................... 381/71.11; 381/71.8; 381/71.1

(58) Field of Search ............................... 381/71.8, 71.11, 381/71.1, 71.4, 71.5, 71.3, 71.14, 71.12; 708/322

(56) References Cited

U.S. PATENT DOCUMENTS 5,018,202 * 5/1991 Takahashi et al. ................ 381/71.11
5,396,561 * 3/1995 Popovich et al. ................. 381/71.11
5,499,302 * 3/1996 Nasami et al. .................... 381/71.11
5,502,869 * 4/1996 Smith et al. ....................... 381/71.3
5,517,571 * 5/1996 Saruta et al. ...................... 381/71.11
5,940,519 * 8/1999 Kuo .................................. 381/71.11
5,991,418 * 11/1999 Kuo .................................. 381/71.11

* cited by examiner

*Primary Examiner*—Vivian Chang
(74) *Attorney, Agent, or Firm*—Robert D. Marshall, Jr.; W. James Brady, III; Frederick J. Telecky, Jr.

(57) ABSTRACT

An off-line modeling system (50) is provided for modeling a feedback path by calculating filter taps. The off-line modeling system (50) includes a reference sensor (16), a secondary source (18), and an off-line modeling circuitry (10). The reference sensor (16) receives a noise signal and a feedback signal (22) and generates a primary signal x(n) in response. The secondary source (18) receives a modeling signal v(n) and provides the modeling signal v(n) to the feedback path. The off-line modeling circuitry (10) includes a signal discrimination circuitry (54), a modeling signal generator (64), a feedback path modeling adaptive filter (60), and associated adaptive algorithm (62) and a summing junction (58). The signal discrimination circuitry (54) receives the primary signal x(n) and generates a modified modeling signal v'(n). The modeling signal generator (64) generates the modeling signal v(n). The feedback path modeling adaptive filter (60) receives the modeling signal v(n) and uses adaptive algorithm (62) to process the modeling signal v(n). In doing this, adaptive algorithm (62) calculates the filter taps. The summing junction (58) subtracts the output signal from the modified modeling signal v'(n) to generate the modeling error signal which is used by the adaptive algorithm (62).

5 Claims, 2 Drawing Sheets

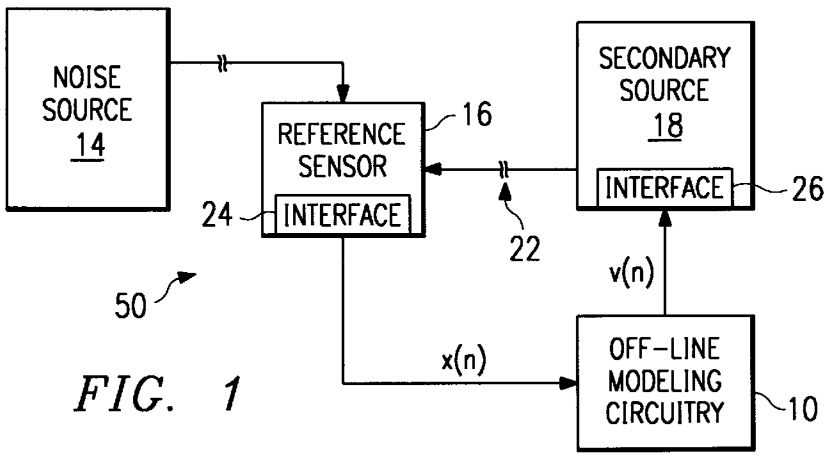
FIG. 1
FIG. 2
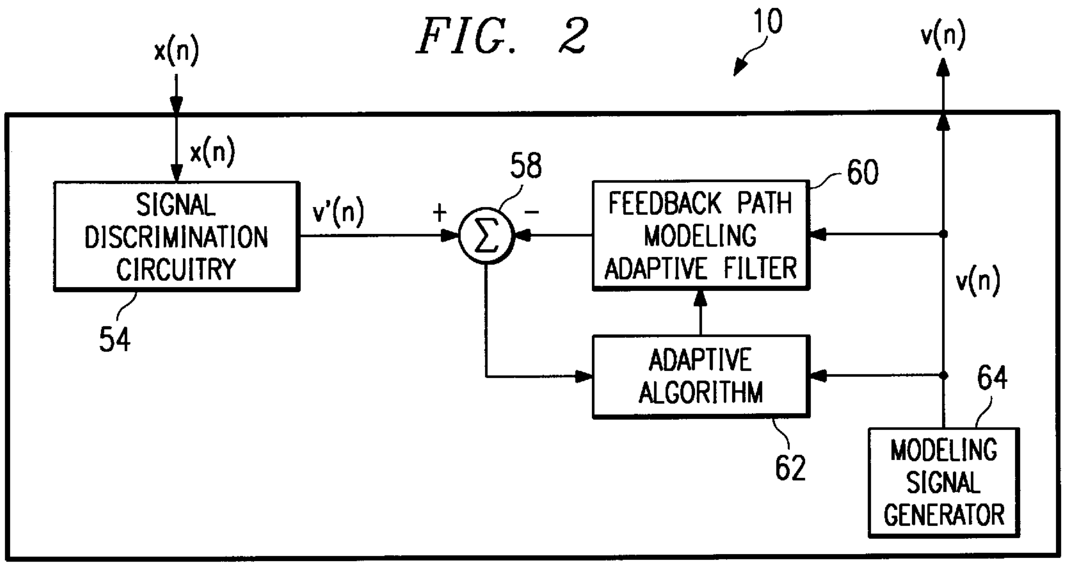
FIG. 3
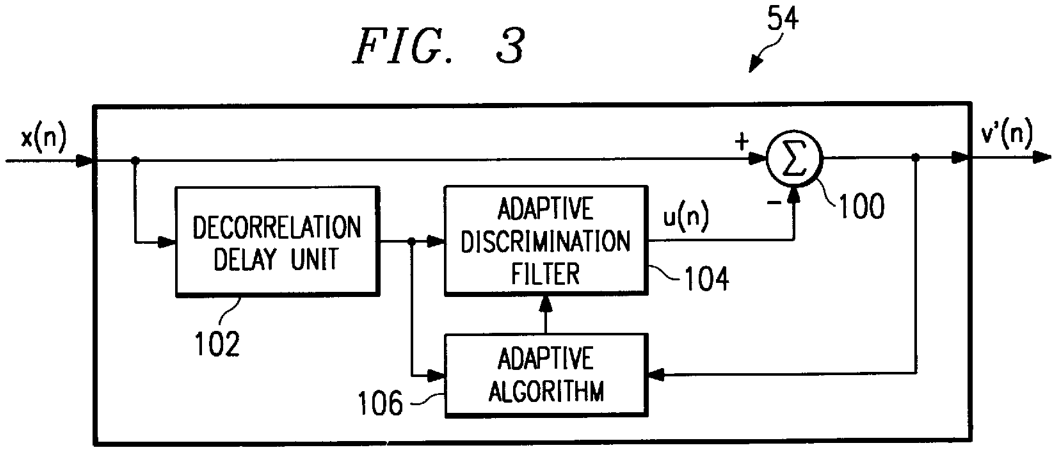

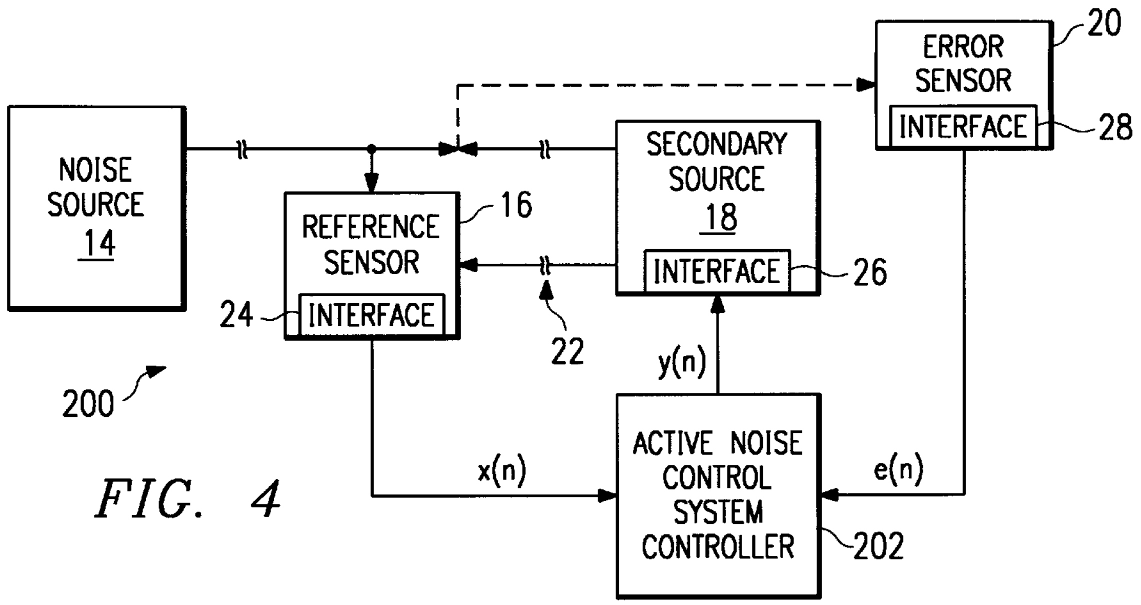
*FIG. 4*
*FIG. 5*
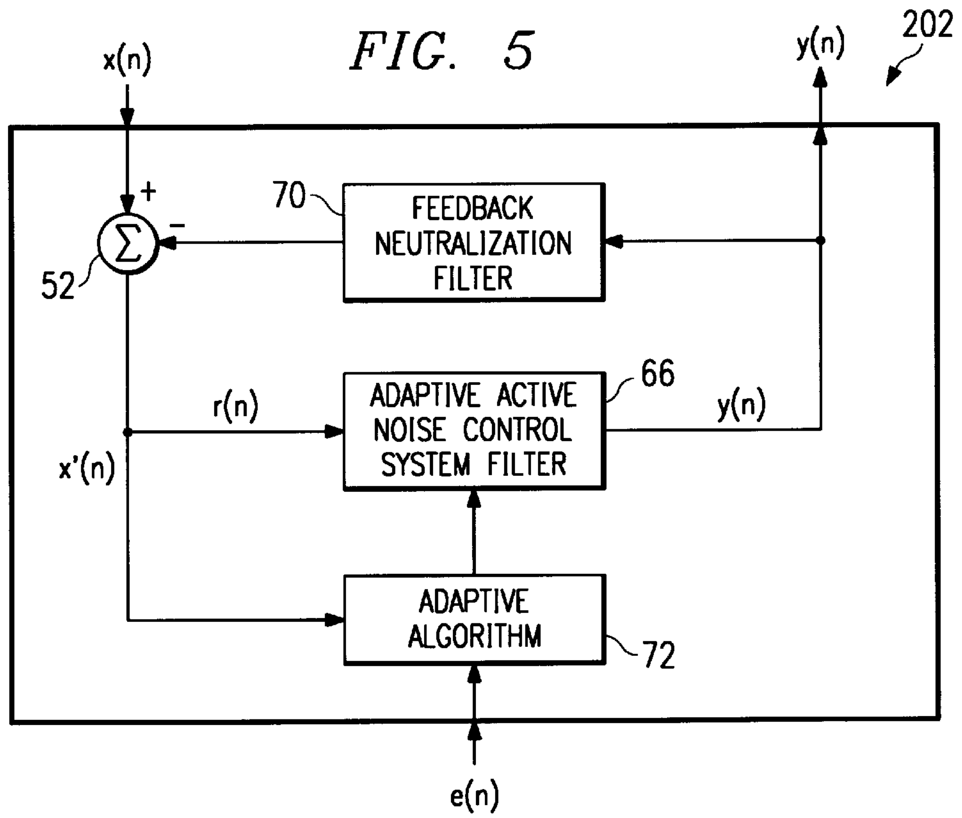

OFF-LINE FEEDBACK PATH MODELING CIRCUITRY AND METHOD FOR OFF-LINE FEEDBACK PATH MODELING

RELATED APPLICATIONS

This application claims priority under 35 U.S.C. 119(e) (1) from U.S. Provisional Patent Application No. 60/033,104 filed Dec. 17, 1996.

This application is related to the following U.S. applications: Ser. No. 08/992,823 entitled Active Noise Control System and Method for On-Line Feedback Path Modeling and On-Line Secondary Path Modeling filed Dec. 17, 1997, claiming priority from U.S. Provisional Patent Application No. 60/033,104 filed Dec. 17, 1996, now U.S. Pat. No. 5,940,519; Ser. No. 08/991,726 entitled Active Noise Control System and Method for On-Line Feedback Path Modeling filed Dec. 17, 1997, claiming priority from U.S. Provisional Patent Application No. 60/033,106 filed Dec. 17, 1996; Ser. No. 08/992,933 entitled Off-Line Path Modeling Circuitry and Method for Off-Line Feedback Path Modeling and Off-Line Secondary Path Modeling filed Dec. 17, 1997, claiming priority from U.S. Provisional Patent Application No. 60/033,107 filed Dec. 17, 1996, now U.S. Pat. No. 5,991,418; and Ser. No. 08/992,777 entitled Digital Hearing Aid and Method for Active Noise Reduction filed Dec. 17, 1997, claiming priority from U.S. Provisional Patent Application No. 60/033,105 filed Dec. 17, 1996. on Dec. 17, 1996.

TECHNICAL FIELD OF THE INVENTION

This invention relates generally to the field of control systems and more particularly to an off-line feedback path modeling circuitry and method for off-line feedback path modeling.

BACKGROUND OF THE INVENTION

Active noise control systems are concerned with the reduction of any type of undesirable disturbance or noise signal provided by a noise source through an environment, whether it is borne by electrical, acoustic, vibration, or any other kind of noise media. Since the noise source and environment are often time-varying, the noise signal will often be non-stationary with respect to frequency content, amplitude, and velocity. Active noise control systems control noise by introducing a canceling "anti-noise" signal into the system environment or media through an appropriate secondary source. The anti-noise signal is ideally of equal amplitude and 180 degrees out of phase with the noise signal. Consequently, the combination of the anti-noise signal with the noise signal at an acoustical summing junction results in the cancellation or attenuation of both signals and hence a reduction in noise.

In order to produce a high degree of noise signal attenuation, the amplitude and phase of both the noise and anti-noise signals must match closely as described above. Generally, this is accomplished by an active noise control system using an active noise control system controller that performs digital signal processing. The digital signal processing is performed using one or more adaptive algorithms for adaptive filtering. The adaptive filtering, and more specifically the adaptive algorithms, track all of the changes in the noise signal and the environment in real-time by minimizing an error signal and continuously tracking time variations of the environment. The adaptive filtering may use any of a variety of known and available adaptive algorithms, such as the least-mean-square ("LMS") algorithm, to establish the taps or coefficients of an associated adaptive filter that models the noise source and environment to reduce or minimize the error or residual signal.

Active noise control systems, as compared to passive noise control systems, provide potential benefits such as reduced size, weight, volume, and cost in addition to improvements in noise attenuation. Active noise control is an effective way to attenuate noise that is often difficult and expensive to control using passive means and has application to a wide variety of problems in manufacturing, industrial operations, and consumer products.

Active noise control systems may generally be divided into feedforward active noise control systems and feedback active noise control systems. The present invention will be illustrated as applied to a feedforward active noise control system and thus the present invention will be described in this context.

A feedforward active noise control system generally includes a reference sensor for sensing a noise signal from a noise source and generating a corresponding primary signal in response; an active noise control system controller for generating a secondary signal; a secondary source, located downstream from the reference sensor, for receiving the secondary signal and generating an anti-noise signal to cancel or attenuate the noise signal; and an error sensor for detecting a residual signal and generating a corresponding error signal in response. The residual signal is equivalent to the difference between the noise signal and the anti-noise signal as provided to the error signal through a primary environment. The active noise control system controller receives the primary signal and the error signal and generates the secondary signal in response.

The active noise control system controller is implemented using a digital signal processor and performs digital signal processing using a specific adaptive filter, depending on the type of cancellation scheme employed, for adaptive filtering. Also, the reference sensor, the secondary source, and the error sensor may include interface circuitry for interfacing with the active noise control system controller. The interface circuitry may include analog-to-digital converters, digital-to-analog converters, analog filters such as low pass filters and automatic gain control amplifiers so that signals can be exchanged in the correct domain, i.e., either the digital or analog domain. The interface circuitry may be provided separately.

Feedforward active noise control systems include a primary path that has a transfer function that may be denoted as $P(z)$. The primary path may be defined as the environment from the reference sensor to the error sensor. Feedforward active noise control systems also include a secondary path and a feedback path. The secondary path has a transfer function that may be denoted as $S(z)$. The secondary path may be defined as the environment from the output of the active noise control system controller to the output of the error sensor. This may include interface circuitry such as a digital-to-analog converter, an analog filter, a power amplifier, a loud speaker, an error microphone, and other devices. The feedback path also has a transfer function and may be denoted by $F(z)$. The feedback path may be defined as the environment from the output of the active noise control system controller to the output of the reference sensor. The active noise control system controller, using a digital signal processor, may include an adaptive filter, that is normally denoted by $W(z)$, that attempts to adaptively model the primary path. The objective of the adaptive filter W(z) is to minimize the residual signal or error signal. The adaptive filtering performed by adaptive filter W(z) may be performed either on-line or off-line.

Feedforward active noise control systems suffer from a serious drawback that often harms overall system performance. Whenever the secondary source generates an anti-noise signal to cancel the noise signal, a portion of the anti-noise signal radiates upstream to the reference sensor where it is received along with the noise signal. The path that the anti-noise signal takes when traveling from the secondary source to the reference sensor is the feedback path. The feedback path, once again, may be defined as the media environment from the output of the active noise control system controller to the output of the reference sensor. The portion of the anti-noise signal flowing to the reference sensor along the feedback path is part of a feedback signal that travels through the feedback path. As a consequence of the feedback signal being received at the reference sensor, an incorrect primary signal is provided to the active noise control system controller by the reference sensor and, hence, overall system performance is harmed. If the feedback signal is in phase with the noise signal, the reference sensor will generate a primary signal that is too large. If the feedback signal is out of phase with the noise signal, the reference senor will also generate a signal that is incorrect. In any event, the feedback signal is undesirable and harms overall performance. The feedback signal may also allow the introduction of poles into the response of the system transfer function which results in potential instability if the gain of the feedback loop becomes large.

In certain applications, overall system performance is significantly degraded if the effects of the feedback path are not modeled and neutralized. The modeling of the feedback path and neutralization of the feedback signal becomes especially critical to overall active noise control system performance in applications in which the secondary source is in close proximity or in close communication with the reference sensor. Such systems would include, for example, appliances such as refrigerators and window air conditioner units in which the air ducts are relatively short. In such applications, the secondary source must be located close to the reference sensor by necessity and hence the feedback signal and its adverse effects will be greater.

The feedback path problem has been recognized in the past and several solutions have been proposed with limited success. A first set of proposed solutions has focused on the use, type, and placement of the reference sensors and the secondary sources, while a second set of proposed solutions has focused on signal processing techniques. The first set of proposed solutions involves the use and placement of directional reference sensors and secondary sources to limit or minimize the feedback signal. These proposed solutions add additional expense and complexity to the system and decrease overall reliability while making it difficult, if not impossible, to obtain good directivity over a broad range of frequencies.

The second set of proposed solutions has focused on signal processing techniques and has achieved limited success. The proposed solutions involving signal processing techniques may be generally separated into off-line modeling techniques and on-line modeling techniques. Both off-line modeling and on-line modeling are system identification techniques in which a signal is provided to the system and the resulting signal is analyzed to construct a model of the unknown system. This is accomplished by exciting an unknown path or environment with the known signal and then measuring or analyzing the resulting signal that is provided in response. The present invention involves off-line modeling, and hence, the problems with prior off-line modeling techniques are discussed below.

Off-line feedback path modeling techniques involve providing a known signal in the absence of the noise signal cancellation that is normally provided by the active noise control system. An adaptive algorithm is used to calculate the coefficients or taps of an adaptive filter to minimize the effects of the feedback path. Once the coefficients or taps are established off-line, the taps or coefficients are fixed in a digital filter and are not changed during actual operation of the active noise control system. Although off-line feedback path modeling techniques are adequate in many systems, off-line modeling may not provide adequate performance when used in a system in which parameters are frequently changing.

Another problem with prior off-line feedback path modeling techniques is the fact that the noise signal must be eliminated or stopped for the off-line feedback path modeling to correctly and quickly model the unknown environment. This is often not practical in many real-world systems. For example, a power transformer that is energized and used to provide power to customers cannot be easily taken out of service so that off-line modeling may take place. In a system that changes frequently, it may be necessary to routinely perform off-line feedback path modeling to update the fixed digital filter taps or coefficients so that the feedback path remains accurately modeled and active noise control system performance remains accurate. In the event that a noise source cannot be shut off, off-line modeling may proceed if the known signal or modeling signal is provided at a very high amplitude for an extended period of time. In spite of this, the off-line model may still be inaccurate due to the presence of the high amplitude modeling signal. The presence of the high amplitude modeling signal also serves as a source of noise during the time that the extended off-line modeling is performed. This is especially troublesome in acoustical systems.

SUMMARY OF THE INVENTION

From the foregoing it may be appreciated that a need has arisen for an off-line feedback path modeling circuitry and method for off-line feedback path modeling that eliminate or reduce the problems described above. In accordance with the present invention, an off-line feedback path modeling circuitry and method for off-line feedback path modeling are provided that provide an off-line modeling signal processing solution to the feedback signal problem. The off-line feedback path modeling circuitry and method of the present invention allow a system to be accurately and quickly modeled without having to eliminate the noise source. The present invention may attenuate both broadband noise signals and narrowband noise signals.

According to an embodiment of the present invention, an off-line modeling system for modeling a feedback path is provided that includes a reference sensor, a secondary source, and an off-line modeling circuitry for modeling the feedback path. The reference sensor receives a noise signal and a feedback signal and generates a primary signal in response. The secondary source receives a modeling signal and provides the modeling signal to the feedback path. In response to providing the modeling signal to the feedback path, the feedback signal is generated. The off-line modeling circuitry includes a signal discrimination circuitry, a modeling signal generator, a feedback path modeling adaptive filter, and a summing junction. The signal discrimination circuitry receives the primary signal and generates a modified modeling signal. The modeling signal generator generates the modeling signal. The feedback path modeling adaptive filter receives the modeling signal and a modeling error signal and uses an adaptive filter to filter the modeling signal to generate an output signal. The adaptive algorithm of the adaptive filter is used to calculate filter taps which are used to model the feedback path. Finally, the summing junction subtracts the output signal from the modified modeling signal to generate the modeling error signal which is used by the adaptive algorithm when calculating the filter taps.

The present invention provides various technical advantages. A technical advantage of the present invention includes the ability to accurately and quickly perform off-line feedback path modeling while a noise source continues to provide a noise signal. This allows for off-line modeling of systems that cannot be practically taken out of service so that off-line modeling may proceed. Because of this, off-line modeling may be performed more frequently to account for any changes in the system environment, such as those caused by temperature and flow changes, that would render the previous off-line model inaccurate or insufficient. Still another technical advantage of the present invention includes the ability to perform off-line modeling using a modeling signal that may be provided at an amplitude that is small in comparison to the noise signal. This allows for increased off-line modeling accuracy while reducing off-line modeling time. Another technical advantage of the present invention includes the ability to implement the present invention using existing digital signal processing techniques and algorithms. Yet another technical advantage of the present invention includes increased active noise control system stability due to the elimination of the feedback path effects. Still another technical advantage of the present invention includes the ability to cancel or attenuate both broadband and narrowband noise signals. Other technical advantages are readily apparent to one skilled in the art from the following FIGUREs, description, and claims.

BRIEF DESCRIPTION OF THE DRAWINGS

For a more complete understanding of the present invention and the advantages thereof, reference is now made to the following brief description, taken in connection with the accompanying drawings and detailed description, wherein like reference numerals represent like parts, in which:

FIG. 1 is a block diagram illustrating an off-line modeling system according to the teachings of the present invention;

FIG. 2 is a block diagram illustrating an off-line modeling circuitry of the off-line modeling system;

FIG. 3 is a block diagram illustrating the signal discrimination circuitry of the off-line modeling circuitry;

FIG. 4 is a feedforward active noise control system according to the teachings of the present invention; and FIG. 5 is a block diagram illustrating an active noise control system controller of the feedforward active noise control system.

DETAILED DESCRIPTION OF THE INVENTION

FIG. 1 is a block diagram of an off-line modeling system 50 that is used to perform off-line feedback path modeling to generate the taps or coefficients that will be used in a feedback neutralization filter. This is illustrated later in FIGS. 4 and 5. Off-line modeling system 50 includes a noise source 14, a reference sensor 16, an off-line modeling circuitry 10, and a secondary source 18. Noise source 14 generates or provides a noise signal through a plant environment where the signal may be received by reference sensor 16. The noise signal is shown flowing from noise source 14 to reference sensor 16 in FIG. 1.

Reference sensor 16 generates a corresponding electronic signal x(n) which may be referred to as a primary signal x(n). Reference sensor 16 may be implemented using virtually any type of sensor such as a microphone, a tachometer, and an accelerometer, to name a few. Reference sensor 16 may also contain an interface circuitry 24 so that the noise signal may be received as an analog signal and the corresponding primary signal x(n) may be generated as a digital signal. Interface circuitry 24 may include any of a variety of devices such as an analog-to-digital converter, an analog filter, an amplifier controlled by an automatic gain control circuit, and any of a variety of other circuitry such as antialiasing circuitry.

Off-line modeling circuitry 10 receives the primary signal x(n) and generates a modeling signal v(n). Modeling signal v(n) is provided to secondary source 18 where it is received and provided back to the plant environment and a feedback path as an analog signal. The feedback path is defined as the path from the output of off-line modeling circuitry 10 to the output of reference sensor 16. Secondary source 18 may be implemented using virtually any signal source such as a speaker, a shaker, or virtually any other available signal source. Secondary source 18 may also include an interface circuitry 26 that allows the modeling signal v(n) to be converted from the digital domain to the analog domain and to be provided at a desired amplitude. Interface circuitry 26 may, for example, include any of variety of circuitry such as a digital-to-analog converter, analog filters, such as a low pass filter, and an amplifier controlled by an automatic gain control circuit.

As a consequence of introducing modeling signal v(n) through the feedback path, a feedback signal 22 flows through the feedback path and excites the feedback path. As a result, feedback signal 22 includes a modified modeling feedback component and is provided to reference sensor 16. Reference sensor 16 receives feedback signal 22 along with the noise signal and generates the primary signal x(n) as a result. Primary signal x(n) will then include a noise signal component and a feedback signal 22 component that includes the modified modeling feedback component.

Interface circuitry 24, and interface circuitry 26 are illustrated in FIG. 1 as being provided as part of their respective sensor and source. However, it should be understood that the interface circuitry may be provided as discrete circuitry components provided independently or separately. The present invention is in no way limited by any one particular type of interface circuitry.

Off-line modeling circuitry 10, illustrated more fully in FIGS. 2 and 3, receives primary signal x(n), which includes the modified modeling feedback component, and uses an adaptive algorithm to generate the taps or coefficients of an adaptive filter which will be used in a later step to neutralize the effects of the feedback path.

Off-line modeling circuitry 10 also includes a modeling signal generator 64 that is used to introduce modeling signal v(n) into off-line modeling system 50 so that the feedback excitation signal or modified modeling feedback component of feedback signal 22 may be generated as a result of modeling signal v(n) having passed through the feedback path. The modified modeling feedback component is the result of modeling signal v(n) becoming correlated to the feedback path as a result of passing through the feedback path. Modeling signal v(n) will generally be provided at an amplitude that is significantly smaller than the noise signal component of primary signal x(n). The modified modeling feedback component, which is provided as feedback signal 22, is used in by off-line modeling circuitry 10 to perform off-line feedback path modeling.

Off-line modeling circuitry 10 may be implemented using digital circuitry such as a digital signal processor. For example, Texas Instruments Incorporated provides a family of digital signal processors including the TMS320C25 and the TMS320C30 digital signal processors. The advent of high-speed digital signal processors and related hardware have made the implementation of the present invention more practical. Many digital signal processors are implemented using a fixed-point data format. In such a case, automatic gain control circuitry must be used at each data input to extend the analog-to-digital converter dynamic range of interface circuitry 24 and interface circuitry 28.

FIG. 2 is a block diagram of off-line modeling circuitry 10. Off-line modeling circuitry 10 includes a signal discrimination circuitry 54, a summing junction 58, a feedback path modeling adaptive filter 60, an adaptive algorithm 62, and a modeling signal generator 64. Off-line modeling circuitry 10 receives primary signal x(n) from reference sensor 16 and performs various modeling functions to generate or calculate the taps or coefficients that may be used to model the feedback path. As mentioned above, these taps or coefficients may be used in a feedback neutralization filter 70 of active noise control system controller 202, as shown in FIG. 5, to eliminate the effects of the feedback path. Off-line modeling circuitry 10 also generates modeling signal v(n) using modeling signal generator 64 which is discussed more fully below. Modeling signal v(n) is provided to secondary source 18.

Signal discrimination circuitry 54 receives primary signal x(n) and generates an output signal v'(n) which may be referred to as a modified modeling feedback signal v'(n). Modified modeling signal v'(n) represents feedback signal 22 which should be equivalent to modeling signal v(n) after having passed through the feedback path. The feedback path, once again, is defined as the plant environment from the output of off-line modeling circuitry 10 to the output of reference sensor 16. Signal discrimination circuitry 54, in effect, extracts the modified modeling feedback component that is included as a component of primary signal x(n). This is accomplished in spite of the fact that the magnitude of modeling signal v(n) will generally be significantly less than the magnitude of the noise signal.

Signal discrimination circuitry 54 uses a decorrelation delay unit and a digital adaptive filter to generate a predicted noise signal u(n) that does not include feedback signal 22. Predicted noise signal u(n) may then be subtracted from primary signal x(n) to generate the modified modeling signal v'(n). Signal discrimination circuitry 54 is illustrated more fully in FIG. 3 and is described in more detail below.

Feedback path modeling adaptive filter 60 and corresponding adaptive algorithm 62 are also provided as part of off-line modeling circuitry 10. Feedback path modeling adaptive filter 60 and adaptive algorithm 62 are used to model the feedback path on an off-line basis and to generate the tap or coefficient settings of feedback path modeling adaptive filter 60 as a result. The feedback path, once again, being defined as the plant environment from the output of the off-line modeling circuitry 10 to the output of reference sensor 16.

Feedback path modeling adaptive filter 60 and adaptive algorithm 62 receive modeling signal v(n) as an input. Adaptive algorithm 62 also receives the output signal of a summing junction 58 as an input. The output signal of summing junction 58 is equivalent to the difference between modified modeling signal v'(n) and the output signal of feedback path modeling adaptive filter 60. The function of adaptive algorithm 62 is to adjust the taps or coefficients of feedback path modeling adaptive filter 60 to minimize the mean-square value of the output signal provided by summing junction 58. The output signal of summing junction 58 may be thought of as an error signal, such as a modeling error signal, to be minimized. Therefore, the filter taps or coefficients are generated so that the error signal is progressively minimized on a sample-by-sample basis.

Feedback path modeling adaptive filter 60 and adaptive algorithm 62 may be implemented as any type of digital adaptive filter, such as an FIR filter or transversal filter, and IIR filter, a lattice filter, a subband filter, or virtually any other digital filter capable of performing adaptive filtering. Preferably, feedback path modeling adaptive filter 60 will be implemented as an FIR filter for increased stability and performance. The adaptive algorithm used in adaptive algorithm 62 may include any known or available adaptive algorithm, such as, for example, a LMS algorithm, a normalized LMS algorithm, a correlation LMS algorithm, a leaky LMS algorithm, a partial-update LMS algorithm, a variable-step-size LMS algorithm, a signed LMS algorithm, or a complex LMS algorithm. Adaptive algorithm 62 may use a recursive or a non-recursive algorithm depending on how feedback path modeling adaptive filter 60 is implemented. For example, if feedback path modeling adaptive filter 60 is implemented as an IIR filter, a recursive LMS algorithm may be used in adaptive algorithm 62. A good overview of the primary adaptive algorithms is provided in Sen M. Kuo & Dennis R. Morgan, *Active Noise Control Systems: Algorithms and DSP Implementations,* (1996). Thus, feedback path modeling adaptive filter 60 and adaptive algorithm 62 provide an off-line feedback path model by calculating the taps or coefficients which represent or model the feedback path.

Modeling signal generator 64 is also provided to generate a white-noise or random signal which serves as modeling signal v(n). Modeling signal generator 64 may use any technique to generate a white-noise, random signal, or chirp signal, but would generally use one of two basic techniques that can be used for random number or chirp signal generation. The first technique uses a lookup table method using a set of stored samples. The second technique uses a signal generation algorithm. Both techniques obtain a sequence that repeats itself after a finite period, and therefore is not truly random for all time. Modeling signal v(n) is provided at secondary source 18 as the output of off-line modeling circuitry 10.

In operation, off-line modeling circuitry 10 receives primary signal x(n) from reference sensor 16 which includes a noise signal component and feedback signal 22 component which includes the modified modeling feedback component. Signal discrimination circuitry 54 receives primary signal x(n) and generates modified modeling signal v'(n) in response. Meanwhile, modeling signal generator 64 provides modeling signal v(n) to feedback path modeling adaptive filter 60 and adaptive algorithm 62, and as an output of off-line modeling circuitry 10. The amplitude of modeling system v(n) will, preferably, be somewhat smaller than the noise signal. This is to allow the modeling signal to excite the feedback path without unduly or significantly affecting the overall plant environment.

Feedback path modeling adaptive filter 60 and adaptive algorithm 62 receive modeling signal v(n) along with the output of summing junction 58 and work together to model the feedback path. In doing this, the appropriate taps or coefficients of feedback path modeling adaptive filter 60 are calculated by adaptive algorithm 62 and stored for later use. The taps or coefficients calculated by adaptive algorithm 62 may be stored in computer memory or any other type of memory or digital circuitry. In any event, the calculated taps or coefficients will be used in feedback neutralization filter 70 of active noise control system controller 202 during active noise control system operation.

FIG. 3 is a block diagram illustrating signal discrimination circuitry 54 that includes a decorrelation delay unit 102, an adaptive discrimination filter 104, an adaptive algorithm 106, and a summing junction 100. Decorrelation delay unit 102 is a digital delay that receives the primary signal x(n) and delays the primary signal x(n) by a selected number of sampling periods. Preferably, decorrelation delay unit 102 provides a delay that is equal to or greater than the delay provided through the feedback path. For example, the time it takes for feedback signal 22 to propagate from the output of off-line modeling circuitry 10 to the output of reference sensor 16 is the delay provided through the feedback path. Although the delay of decorrelation delay unit 102 is preferably set at a delay that is equal to or greater than the delay of the feedback path, performance is enhanced even with a delay time as short as one sample period. Thus, the present invention encompasses a delay of one sample period or more.

Adaptive discrimination filter 104 and adaptive algorithm 106 both receive the output signal from decorrelation delay unit 102. Adaptive algorithm 106 also receives modified modeling signal v'(n) as an input signal and uses this as an error signal. Adaptive algorithm 106 calculates the taps or coefficients for adaptive discrimination filter 104 that will minimize the modified modeling signal v'(n). In response, adaptive discrimination filter 104 receives the output of decorrelation delay unit 102 and generates predicted noise signal u(n) which, ideally, is equivalent to the actual noise signal. Thus, the modified modeling feedback component, or feedback signal 22, is removed and the predicted noise signal u(n) is provided to summing junction 100 where it is subtracted from the primary signal x(n) to generate modified modeling signal v'(n) by removing the noise signal component of the primary signal x(n).

Adaptive algorithm 106 may be implemented using any of a variety of known and available adaptive algorithms such as those described previously in connection with adaptive algorithm 62. Adaptive discrimination filter 104 may be any type of digital filters such as an FIR or an IIR filter. Decorrelation delay unit 102 may be implemented using a computer memory or register so that a desired delay in primary signal x(n) may be provided to decorrelate the modified modeling feedback component of primary signal x(n) while leaving the narrowband components correlated. As a consequence of the delay, adaptive discrimination filter 104 will only be able to predict or generate the signal components that remain correlated.

FIG. 4 is a block diagram of a feedforward active noise control system 200 operating to cancel a noise signal provided by noise source 14 while performing feedback neutralization using the coefficients or taps calculated off-line as discussed above. Feedforward active noise control system 200 includes noise source 14, reference sensor 16, an active noise control system controller 202, secondary source 18, and an error sensor 20. Noise source 14 generates or provides the noise signal through a plant environment where the signal may be received by reference sensor 16. The noise signal is shown flowing from noise source 14. Reference sensor 16 generates primary signal x(n) in response to receiving the noise signal.

Active noise control system controller 10 receives the primary signal x(n) and generates a corresponding electrical signal y(n), which may be referred to as a secondary signal y(n). The secondary signal y(n) is provided to secondary source 18 where it is received and provided back to the plant environment as an analog signal. The output signal of secondary source 18 may be referred to as an anti-noise signal and is designed to reduce, cancel, or neutralize the noise signal provided by noise source 14.

As a consequence of introducing the anti-noise signal into the plant environment, a portion of the anti-noise signal also travels back to reference sensor 16 along the feedback path which is defined, here, as the path from the output of active noise control system controller 202 to the output of reference sensor 16. Feedback signal 22 is shown flowing through the feedback path and includes, in this case, the portion of the anti-noise signal that is provided along the feedback path that may be referred to as an anti-noise feedback component. Reference sensor 16 receives feedback signal 22 along with the noise signal and generates the primary signal x(n) as a result. Primary signal x(n) will then include a noise signal component and the anti-noise feedback component. Without subsequent neutralization, the introduction of feedback signal 22 to the input of reference sensor 16 results in the generation of an incorrect primary signal x(n).

Error sensor 20 receives a residual signal that is the result of the combination of the noise signal and the anti-noise signal at an acoustical summing junction in the plant environment. The residual signal is ideally zero. The residual signal is zero when the anti-noise signal is provided at the acoustical summing junction at an amplitude equivalent to the noise signal but 180 degrees out of phase with the noise signal and entirely cancels the noise signal.

Error sensor 20 receives the residual signal and generates a corresponding error signal e(n). Error sensor 20 may be implemented using virtually any sensor. For example, error sensor 20, just as with reference sensor 16, may be implemented using a microphone, a tachometer, an accelerometer, or virtually any other available sensor. Error signal e(n) may be provided in the digital domain through the use of an interface circuitry 28. Interface circuitry 28 may be similar to interface circuitry 24 and may include such circuitry as an analog-to-digital converter, a smoothing filter, and an amplifier controlled by an automatic gain control circuit. Although interface circuitry 28 is illustrated in FIG. 4 as being provided as part of error sensor 20, it should be understood that interface circuitry 28 may be provided as discrete circuitry components which are provided independently or separately. The present invention is in no way limited to any one particular type of interface circuitry 28.

Error signal e(n) is provided to active noise control system controller 202 where it is received and used by an adaptive active noise control system filter 66 to provide active noise control so that the generation of the secondary signal y(n) may be adjusted as the noise signal changes or as the primary plant or environment changes. This improves overall performance of feedforward active noise control system 200. Adaptive active noise control system filter 66 is the main filter of active noise control system controller 202 and is illustrated in FIG. 5 and described more fully below.

In operation, active noise control system controller 202 receives primary signal x(n) and error signal e(n) and generates secondary signal y(n) in response to cancel the noise signal. Active noise control system controller 202 includes feedback signal neutralization circuitry and adaptive system filter circuitry for adaptively modeling the primary plant or environment which has a transfer function denoted by P(z). Active noise control system controller 202 receives the primary signal x(n) and removes the anti-noise feedback component using a feedback neutralization filter that uses the coefficients or taps calculated during off-line feedback path modeling as discussed above and as illustrated in FIGS. 1 through 3. After removing the anti-noise feedback component, the remaining signal is processed using an adaptive active noise control system filter and associated adaptive algorithm so that secondary signal y(n) is generated at a value to cancel the noise signal. The error signal e(n) is used by the adaptive algorithm in generating secondary signal y(n).

Active noise control system controller 202 may be implemented using digital circuitry such as a digital signal processor. As mentioned above, Texas Instruments Incorporated provides a family of digital signal processors including the TMS320C25 and the TMS320C30 digital signal processors. The advent of high-speed digital signal processors and related hardware have made the implementation of the present invention more practical. Many digital signal processors are implemented using a fixed-point data format. In such a case, automatic gain control circuitry must be used at each data input to extend the analog-to-digital converter dynamic range of interface circuitry 24 and interface circuitry 28.

FIG. 5 is a block diagram of active noise control system controller 202. Active noise control system controller 202 includes a summing junction 52, feedback neutralization filter 70, adaptive active noise control system filter 66, and corresponding adaptive algorithm 72. Active noise control system controller 202 receives primary signal x(n) from reference sensor 16 and error signal e(n) from error sensor 20 and performs various filtering, processing, and modeling functions to generate secondary signal y(n) which is provided to secondary source 18.

Primary signal x(n) is received at summing junction 52 along with the output signal of feedback neutralization filter 70. Summing junction 52 subtracts the output signal of feedback neutralization filter 70 from primary signal x(n) to generate an output signal x'(n) in response. The output signal x'(n) may be referred to as a feedback neutralized primary signal x'(n) since the anti-noise feedback component of feedback signal 22, which is provided as a component of primary signal x(n), is removed by feedback neutralization filter 70. Feedback neutralization filter 70 will generally be implemented as a digital filter with fixed coefficient or taps. However, the fixed coefficients or taps may be changed after off-line feedback path modeling has been performed such as that described above and as illustrated in FIGS. 1 through 3. As a result of performing the off-line feedback path modeling, feedback neutralization filter 70 receives the calculated taps or coefficients and uses these taps to generate its output signal. It should be understood that during active noise control system operation, the taps or coefficients of feedback neutralization filter 70 generally do not change.

Feedback neutralized primary signal x'(n), which contains the noise signal component of primary signal x(n), is received by adaptive active noise control system filter 66 and adaptive algorithm 72. Adaptive active noise control system filter 66 and adaptive algorithm 72 function together to generate secondary signal y(n). Adaptive active noise control system filter 66 receives feedback neutralized primary signal x'(n) while adaptive algorithm 72 receives both feedback neutralized signal x'(n) and error signal e(n). Adaptive algorithm 72 generates coefficients or taps that are used by adaptive active noise control system filter 66 to generate secondary signal y(n) at an appropriate value to cancel the noise signal. Adaptive algorithm 72 generates the taps or coefficients that will minimize the value of error signal e(n).

Adaptive active noise control system filter 66 may be implemented as any type of digital adaptive filter, such as those discussed previously with respect to feedback path modeling adaptive filter 60 which is illustrated in FIG. 2. Preferably, adaptive active noise control system filter 66 will be implemented as an FIR filter for increased stability and performance. Similarly, the adaptive algorithm used by adaptive algorithm 72 may include any known or available adaptive algorithms such as, for example, a least mean-square (LMS) algorithm, a normalized LMS algorithm, a correlation LMS algorithm, a leaky LMS algorithm, a partial-update LMS algorithm, a variable-step-size LMS algorithm, a signed LMS algorithm, or a complex LMS algorithm. Adaptive algorithm 72 may use a recursive or a non-recursive algorithm depending on how adaptive active noise control system filter 66 is implemented. For example, if adaptive active noise control system filter 66 is implemented as an IIR filter, a recursive LMS algorithm may be used in adaptive algorithm 72.

Feedback neutralization filter 70 is a non-adaptive digital filter and receives the tap or coefficient settings that were previously calculated off-line by adaptive algorithm 62 of off-line modeling circuitry 10. Feedback neutralization filter 70 receives secondary signal y(n) from adaptive active noise control system filter 66 and filters this signal to generate an output signal that is about equivalent to the anti-noise feedback component of primary signal x(n). The output signal of feedback neutralization filter 70 is then provided to summing junction 52 where the anti-noise feedback component is removed from primary signal x(n).

In operation, active noise control system controller 202 receives primary signal x(n) from reference sensor 16 along with error signal e(n) from error sensor 20. Primary signal x(n) may be thought of as containing a noise signal component and an anti-noise feedback component. The primary signal x(n) passes through summing junction 52 where the anti-noise feedback component of feedback signal 22 is removed by feedback neutralized filter 70 to generate feedback neutralized primary signal x'(n).

Feedback neutralized primary signal x'(n) is then provided to both adaptive active noise control system filter 66 and adaptive algorithm 72. Adaptive algorithm 72 also receives error signal e(n) from error sensor 20. Adaptive active noise control system filter 66 generates secondary signal y(n) in response. Adaptive algorithm 72 calculates and adjusts the coefficients or taps of adaptive active noise control system filter 66 to minimize error signal e(n). Ideally, secondary signal y(n) is about equal to a signal that is 180 degrees out of phase with the noise signal so that the noise signal will be canceled when combined with secondary signal y(n) after it is converted to the analog domain by secondary source 18. Thus, active noise control system controller 202 controls feedforward active noise control system 200 by generating secondary signal y(n) so that the noise signal may be attenuated or canceled while also providing feedback path neutralization circuitry to eliminate any adverse effects caused by the presence of the feedback path. Active noise control system controller 202 allows for the cancellation of both narrowband and broadband noise signals.

Thus, it is apparent that there has been provided, in accordance with the present invention, an off-line feedback path modeling circuitry and method for off-line feedback path modeling that eliminate or reduce the adverse effects of the feedback path on overall system operation and that satisfy the advantages set forth above. Although the preferred embodiment has been described in detail, it should be understood that various changes, substitutions, and alterations can be made herein without departing from the scope of the present invention. It should also be understood that the present invention may be implemented to reduce any noise source including, but not limited to, vibrations, acoustical signals, electrical signals, and the like. The circuits and functional blocks described and illustrated in the preferred embodiment as discrete or separate circuits or functional blocks may be combined into one or split into separate circuits or functional blocks without departing from the scope of the present invention. Furthermore, the direct connections illustrated herein could be altered by one skilled in the art such that two circuits or functional blocks are merely coupled to one another through an intermediate circuit or functional block without being directly connected while still achieving the desired results demonstrated by the present invention. Other examples of changes, substitutions, and alterations are readily ascertainable by one skilled in the art and could be made without departing from the spirit and scope of the present invention as defined by the following claims.

What is claimed is:

1. An off-line modeling system for modeling a feedback path by calculating filter taps, the off-line modeling system comprising:

a reference sensor operable to receive a noise signal and a feedback signal and to generate a primary signal in response;

a secondary source operable to receive a modeling signal and to provide the modeling signal to the feedback path; and an off-line modeling circuitry for modeling the feedback path including:

a signal discrimination circuitry operable to receive the primary signal and to generate a modified modeling signal, said signal discrimination circuitry including:

a decorrelation delay unit operable to delay the primary signal and to generate an output signal that corresponds to a delayed primary signal, an adaptive discrimination filter operable to receive the output signal and the modified modeling signal and to filter the output signal to generate a predicted noise signal, and a second summing junction operable to subtract the predicted noise signal from the primary signal to generate the modified modeling signal, a modeling signal generator operable to generate the modeling signal, a feedback path modeling adaptive filter operable to receive the modeling signal and a modeling error signal and to filter the modeling signal to generate an output signal and to calculate the filter taps, and a summing junction operable to subtract the output signal from the modified modeling signal to generate the modeling error signal which is provided to an adaptive algorithm used by the feedback path modeling adaptive filter.

2. An off-line modeling circuitry for modeling the feedback path of an active noise control system, the off-line modeling circuitry comprising:

a signal discrimination circuitry operable to receive a primary signal and to generate a modified modeling signal, said signal discrimination circuitry including:

a decorrelation delay unit operable to delay the primary signal and to generate an output signal that corresponds to a delayed primary signal, an adaptive discrimination filter operable to receive the output signal and the modified modeling signal and to filter the output signal to generate a predicted noise signal, and a second summing junction operable to subtract the predicted noise signal from the primary signal to generate the modified modeling signal;

a modeling signal generator operable to generate a modeling signal;

a feedback path modeling adaptive filter operable to receive the modeling signal and a modeling error signal and to filter the modeling signal to generate an output signal and to generate filter taps; and a summing junction operable to subtract the output signal from the modified modeling signal to generate the modeling error signal which is provided to an adaptive algorithm used by the feedback path modeling adaptive filter.

3. The off-line modeling circuitry of claim 2, wherein the delay of the decorrelation delay unit is a programmable delay.

4. The off-line modeling circuitry of claim 2, wherein the delay is equal to or greater than the delay of the feedback path being modeled.

5. A method for off-line feedback path modeling comprising the steps of:

generating a modeling signal and providing to an environment;

receiving a primary signal from the environment;

generating a modified modeling signal using the primary signal and a digital delay that is equal to or greater than the delay of the feedback path being modeled; and generating filter taps for use in a feedback neutralization filter by adaptively filtering the modeling signal using an adaptive filter and the modified modeling signal.

* * * * *